(12) United States Patent
Drennen, III et al.

(10) Patent No.: US 7,528,950 B2
(45) Date of Patent: *May 5, 2009

(54) TUNABLE LASER-BASED PROCESS MONITORING APPARATUS

(75) Inventors: James K. Drennen, III, Mars, PA (US); Carl A. Anderson, Cranberry Township, PA (US); Robert P. Cogdill, Pittsburgh, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/033,332

(22) Filed: Jan. 11, 2005

(65) Prior Publication Data

US 2006/0152729 A1    Jul. 13, 2006

(51) Int. Cl.
 *G01J 3/42* (2006.01)
(52) U.S. Cl. .......... 356/320; 250/205; 250/339.02; 250/339.07
(58) Field of Classification Search ........ 356/432, 356/433, 435, 446, 448, 300, 301; 250/339.01, 250/339.02, 339.07
See application file for complete search history.

(56) References Cited

U.S. PATENT DOCUMENTS

| | | | | |
|---|---|---|---|---|
| 4,124,803 A | * | 11/1978 | Bowers | 250/559.09 |
| 4,176,963 A | * | 12/1979 | Fabinski et al. | 356/418 |
| 5,339,151 A | * | 8/1994 | Shinn | 356/328 |
| 5,473,437 A | | 12/1995 | Blumenfeld et al. | |
| 5,533,139 A | * | 7/1996 | Parker et al. | 382/108 |
| 6,040,914 A | | 3/2000 | Bortz et al. | |
| 6,134,000 A | | 10/2000 | Schmid et al. | |
| 6,522,402 B1 | | 2/2003 | Wang et al. | |
| 6,608,847 B2 | | 8/2003 | Zhang et al. | |
| 6,639,678 B1 | | 10/2003 | Veale et al. | |
| 2002/0113210 A1 | * | 8/2002 | Treado et al. | 250/331 |
| 2004/0084623 A1 | | 5/2004 | Long et al. | |
| 2005/0213089 A1 | | 9/2005 | Margalith et al. | |

* cited by examiner

*Primary Examiner*—Gregory J Toatley, Jr.
*Assistant Examiner*—Juan D Valentin
(74) *Attorney, Agent, or Firm*—Buchanan Ingersoll & Rooney PC; Craig G. Cochenour

(57) ABSTRACT

A chemical imaging and process monitoring device which utilizes a computer controlled tunable laser to provide light at discrete wavelengths in the near infrared band and a focal plane array to image or a single-point photo detector to detect the intensity of light reflected from a sample illuminated at various wavelengths of light. The device also provides light intensity reference detectors at the source and terminus of the light delivery pathway for normalizing the collected data and for detecting defects in the light delivery pathway.

30 Claims, 4 Drawing Sheets

TUNABLE LASER-BASED PROCESS MONITORING APPARATUS

FIELD OF THE INVENTION

This invention relates to the field of chemical imaging of samples, and, in particular, to chemical sampling, spectroscopic data collection, and imaging of samples illuminated by light of varying wavelengths in the near-infrared range.

BACKGROUND OF THE INVENTION

Chemical imaging is a well-known method for obtaining information about the molecular makeup of a particular material that combines digital imaging and near-infrared (NIR) spectroscopy, or other spectroscopic techniques. By illuminating the material with light of a particular wavelength, or with a broadband illumination source, and observing the light reflected or transmitted by the material at various wavelengths, it is possible to determine the composition of the material, as is well known in the art. By utilizing digital imagery in combination with NIR spectroscopy, it is possible to obtain two or three dimensional data structures which can be converted into chemical images of the surface of the sample.

The chemical imaging method includes delivering narrow band or broadband radiation to a sample and collecting the radiation that is either reflected from or transmitted through the sample via a focal plane array, a camera or raster scanned detector to yield a spectral image by modulating either the wavelength of the illumination source or the center wavelength of interference filters placed between the sample and the image detector. A complete spectral image hypercube of a sample is thus acquired in steps, wherein each pixel of the hypercube contains the optical intensity spectrum across the sample wavelength range for a specific X-Y position.

Prior art chemical imaging methods and apparatus consisted of taking point-by-point spectra of a small region of the surface of a sample and rasterizing the spectra to obtain the chemical image. This method is time-consuming and cumbersome, in that many point spectra must be collected to make a chemical image of desirable resolution.

Alternatively, chemical images may be collected using a CCD or focal plane array to collect the image over the entire desired area. Such a system is described in U.S. Pat. No. 6,734,932 (Treado, et al.), entitled "Near Infrared Chemical Imaging Microscope". The Treado imager is an interferometric type imager which utilizes a broadband NIR or white-light illumination source, a tunable filter, such as a liquid crystal tunable filter (LCTF) or an acousto-optic tunable filter (AOTF) for wavelength discrimination, and a CCD or FPA for image capture. This type of imager, however, suffers from several drawbacks. First, broadband source illumination and inefficient light collection can have an adverse impact on the signal-to-noise ratio of the imager. Constant, broadband illumination can also often be damaging to labile samples, for example, biological specimens, thereby limiting the application of the device. Interferometric-type imagers are also limited in their ability to operate in alternative modes. For example, it is difficult to perform Stokes vibrational circular dichroism (VCD) spectroscopy, with an interferometric-type imager because the signal-to-noise ratio (SNR), optical geometry, and acquisition speed are prohibitive. Lastly, the collection of reference images for the normalization of collected chemical images can be time-consuming and cumbersome, requiring the collection of a reference image at the tunable filter for each wavelength interval of interest.

Tuned illumination type imagers are also known in the art. These type of imagers function by illuminating the samples with light of a single wavelength or a weighted combination of multiple spectral bands. Detection using these types of imagers is simplified because the need for the interferometric element (i.e., the tunable filter) is eliminated. Beam delivery is also simplified by the use of fiber optic and hollow waveguide technology. Current, prior art tuned illumination imagers utilize grating monochrometers, LEDs or laser diodes to provide single or very narrow-band wavelength illumination. Such a device is disclosed in U.S. Pat. No. 6,690,466 (Miller, et al.), entitled "Spectral Imaging System," in which the tuned illumination source consists of an array of LEDs, with one LED per spectral channel.

SUMMARY OF THE INVENTION

The chemical imaging apparatus of the present invention is a tunable illumination type imager which utilizes an actively tuned source illumination, in this case, a tunable near infrared laser. The use of the tunable laser in this context is novel in the art and represents an improvement over current prior art tunable illumination devices, many of which utilize discrete LEDs or laser diodes for illumination. Further improvements over the current state of the prior art include the use of one or more reference detectors in the illumination delivery path, which obviates the need for the collection of reference samples at the point of illumination. Reference detectors are also useful for providing a self-diagnostic function to detect changes in the illumination source or defects in the optical pathway between the source of illumination and the point of illumination of the sample. The device is also easily configurable to operate in either reflectance or transmission modes and can be easily retrofitted with optical filters and polarizers for use in Raman, laser induced fluorescence and polarimetry measurements.

In a second embodiment of the invention, the tunable laser system may be used to monitor manufacturing processes in which it is necessary to monitor the quality of a fungible commodity. In this embodiment, the imaging apparatus is replaced with a single-point photo detector which is capable of measuring the intensity of light reflected from a sample of the commodity when illuminated by various wavelengths of infrared light. This is particularly useful in the petroleum, food and pharmaceutical industries, in which specific formulations of products will have a unique chemical signature in response to a stimulus consisting of infrared light within a specific bandwidth.

DETAILED DESCRIPTION OF THE INVENTION

Figure 1:
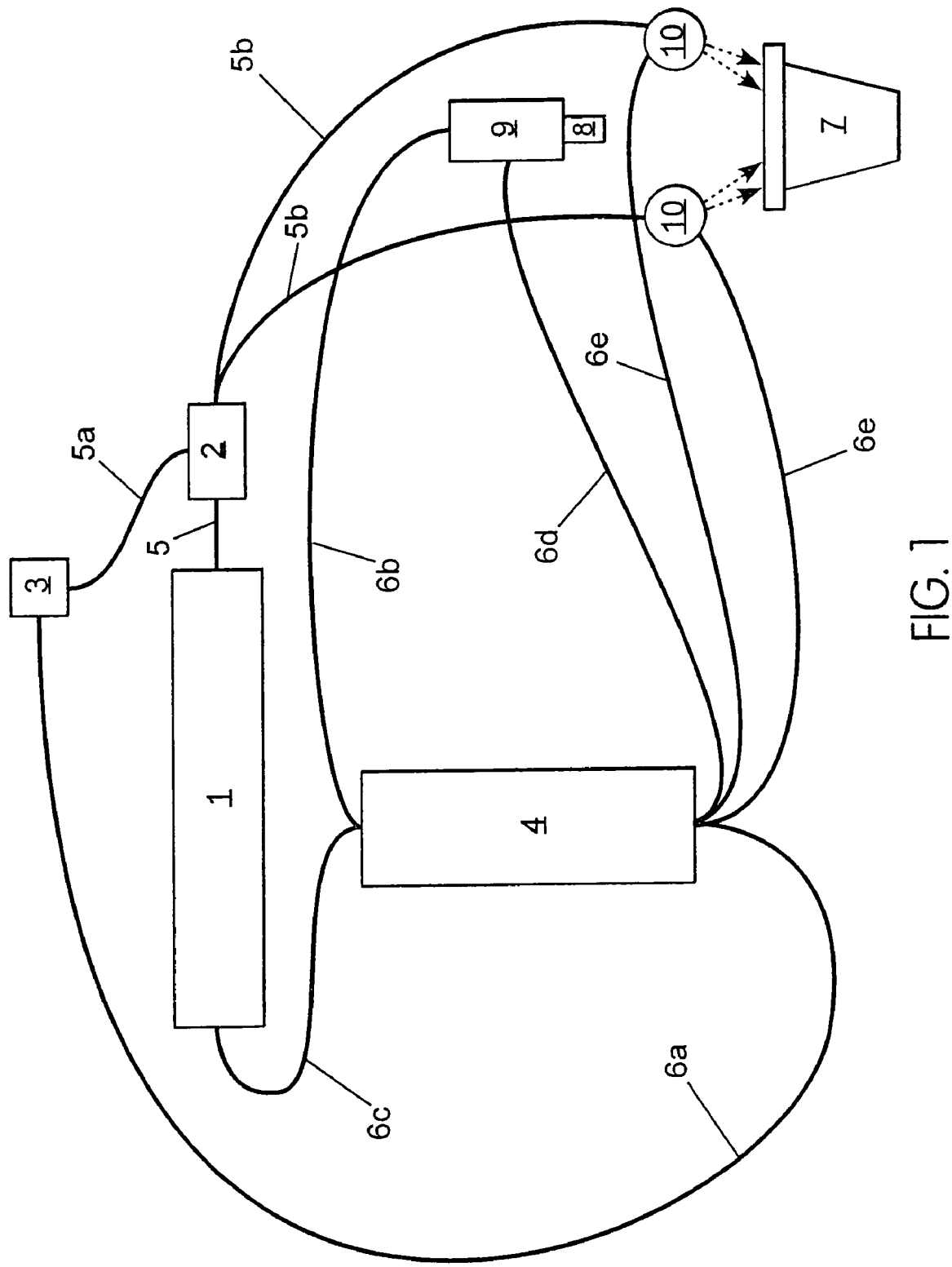
FIG. 1 is a schematic representation of the imaging apparatus of the present invention configured for performing reflectance imaging.

The preferred embodiment of the invention is shown in schematic representation in FIG. 1. Reference No. 1 is a tunable illumination source, preferably a near infrared (wavelengths approximately 700 to 2500 nm) tunable laser of a type such as that made by Opotek Corporation of Carlsbad, Calif. In an alternate embodiment, the tunable laser can be replaced with a tunable illumination source capable of providing illumination over a broader range of wavelengths, including visible and ultraviolet illumination. Preferably, the tunable laser is able to be tuned to individual wavelengths with a resolution of 10 cm$^{-1}$, with a tuning resolution that is adjustable depending on the analytical need, and is not less than 5 cm$^{-1}$. Preferably, tunable laser 1 can be tuned via a computer controlled interface.

Fiber optic cable 5 delivers the output of tunable laser 1 to a beam splitter 2. Beam splitter 2 is preferably a polarizing beam splitter of the type sold by Control Optics of Ontario, Canada. The tuned illumination generated by tunable laser 1 is split at beam splitter 2, with one leg of the split being delivered via fiber optic cable 5a to reference detector 3, and the other leg of the split being delivered to fiber terminus 10 through fiber optic cable 5b. In reflectance mode, where illumination from multiple sources is desired to reduce shadow effects, multiple beam splitters may be necessary. Therefore, in the schematic representation shown in FIG. 1, beam splitter 2 would, in reality, consist of two discrete physical beam splitters.

Figure 3:
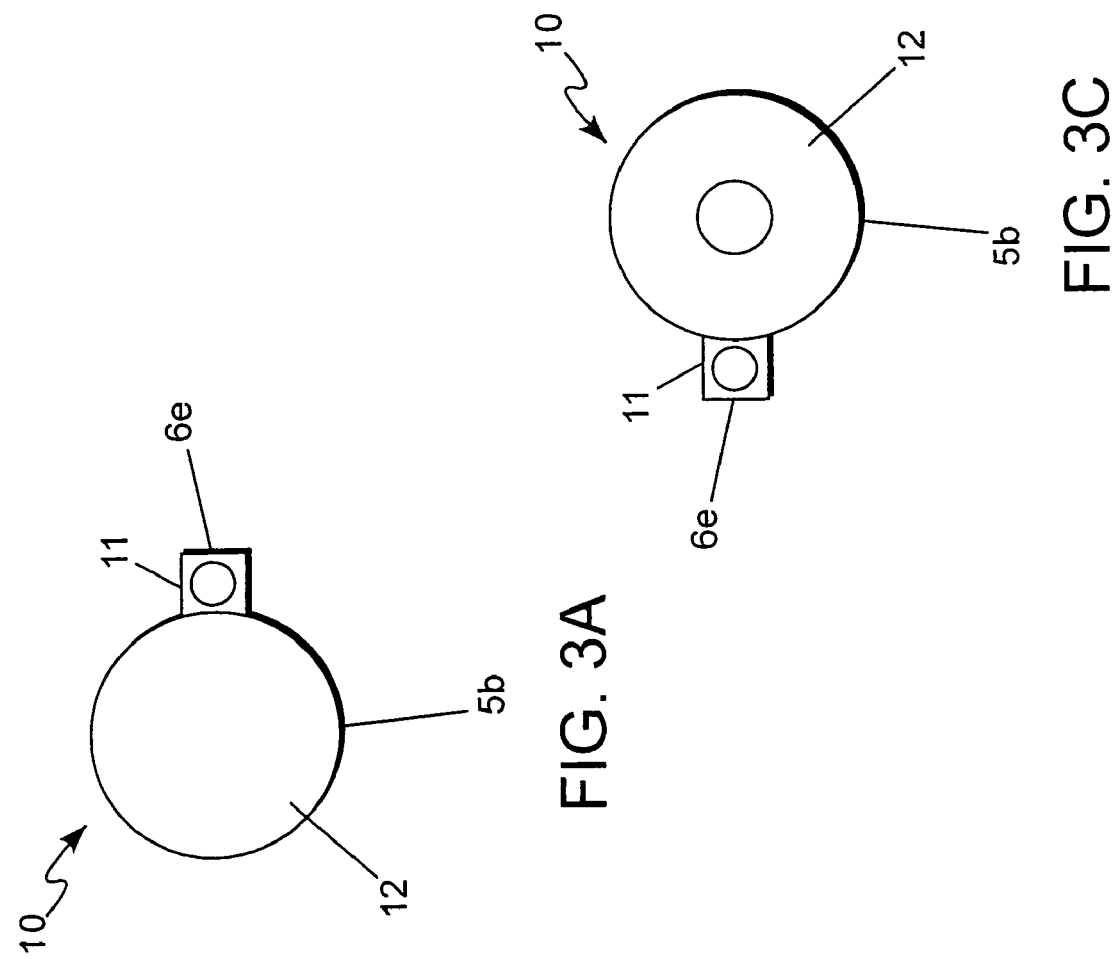
FIGS. 3a, 3b, and 3c provide back, side, and front views respectively of the fiber terminus having an integrated detector therewith.

The details of fiber terminus 10 with integrated detector 11 are shown in FIGS. 3a, 3b, and 3c, showing fiber terminus 10 in back, side, and front views, respectively. Fiber terminus 10 consists of integrating sphere 12, preferably of the type model IS-010sold by Pro-Lite Technology of the United Kingdom. Integrating sphere 12 serves to provide a highly uniform illumination pattern across the surface of the sample. Fiber terminus 10 also includes integrated detector 11. Integrated detector 11 is a simple photovoltaic detector, preferably a mercury cadmium telluride (MCT) photovoltaic detector, and may include an analog-to-digital converter (ADC) for converting analog illumination intensity information into digital form, which may be returned to computer 4 via cable 6e.

Figure 2:
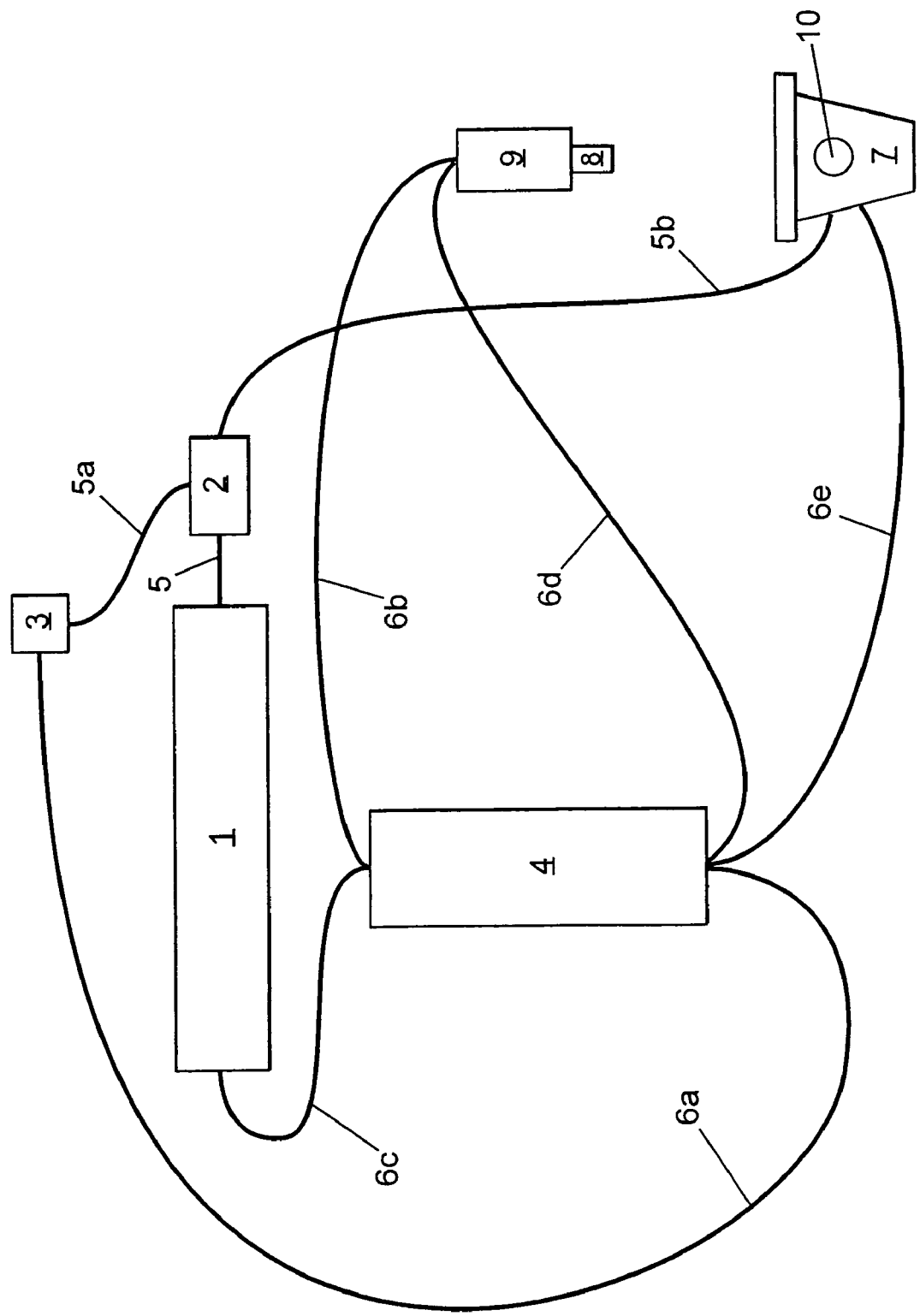
FIG. 2 is a schematic representation of the imaging apparatus of the present invention configured for transmission imaging.

The device can be configured to operate in reflectance mode, as shown in FIG. 1, or in transmission mode, as shown in FIG. 2. In the reflectance configuration shown in FIG. 1, multiple fiber terminals 10 are shown to provide general all around illumination and to eliminate or limit shadow effects with respect to a sample, which is positioned on stage 7. Camera 9 is configured to collect light which is reflected from the sample. In transmission configuration, shown in FIG. 2, a single fiber terminus 10 is utilized and is positioned under stage 7 such that the light emitted therefrom will be transmitted through the sample to camera 9, positioned above the sample, to collect light which is transmitted through the sample.

Camera 9 is preferably a near infrared (NIR) camera utilizing an MCT based focal plane array sensor, but any camera capable of digitizing an image in the NIR wavelength range can be used. Camera 9 is fitted with objective 8, which is preferably an achromatic lens or wavefront coded lens. Other optical elements may also be used in conjunction with camera objective 8, including optical filters and polarizers (not shown) for use in various alternative types of imaging, including VCD, Raman, and laser induced fluorescence.

Computer 4 is a standard personal type computer which provides control of all components of the imager. Computer 4 is able to control the wavelength at which tunable illumination source 1 emits light via cable 6c. In addition, computer 4 is able to control infrared camera 9 via control cable 6b. Digital image data collected by camera 9 is returned to computer 4 via cable 6d for formatting and storage.

The other function of computer 4 is to provide normalization of the collected data and error detection for the overall process. Reference detector 3 is preferably an MCT photovoltaic detector capable of detecting the intensity of the tuned illumination delivered via fiber optic cable 5a. Analog-to-digital conversion (ADC) and temperature controls are co-located with the reference detectors to prevent signal contamination from external electromagnetic noise sources. The digital information is sent via data cable 6a to computer 4 and image data collected from camera 9 via cable 6d is normalized by computer 4 with respect to the intensity of the illuminating light as provided by reference detector 3. Mathematically, the measured intensity at each pixel will be compared to the value of the illumination at reference detector 3 by use of a mathematical function (e.g. pixel intensity/reference detector intensity) for the wavelength of light being measured. In this fashion, each plane (wavelength) of data within the spectral hypercube will be normalized to the reference value. This is a novel feature which provides real time collection of reference values, eliminating the need to collect individual reference images by imaging a reference sample at each wavelength. Reference detectors 11, located at fiber terminals 10 may also be used for this function, with the data being returned to computer 4 via cable 6e. When using reference detectors 11 for this purpose, the measured intensity at each pixel will be divided by the mean of the output of the multiple fiber terminus reference detectors 11 for the wavelength of light being measured. As such, each plane of data within the spectral hypercube will be normalized to the intensity of the light measured at fiber terminus reference detectors 11. This feature alone provides a significant reduction in the time necessary to perform the chemical imaging over known prior art systems.

Reference detectors 11 may also be used as a self-diagnosis tool to detect defects or changes in the optical path. Reference detectors 11 collect information regarding the intensity of the beam which is delivered to the sample and it is compared to the intensity of the beam collected by reference detector 3 by computer 4 to ensure that degradation of the light source between splitter 2 and fiber terminus 10 has not occurred. Ideally, the relative intensity ratio of the light at fiber terminus 10 to the light at reference detector 3 should remain constant.

The imager of the present invention is also capable of self correcting for noise induced in the collected spectrum by operating inefficiencies inherent in the components. To do this, an image is collected absent illumination, and the "dark" image is subsequently subtracted from images collected under illumination. The "dark" noise is subtracted from reference detectors 10 and 3 in a similar fashion. Noise can therefore be detected with pixel-level resolution and automatic compensation applied, such that a normalized image corrected for induced noise could be calculated on a pixel-by-pixel basis using the general formula ($P_{sample\ image} - P_{dark\ image}$)/(reference value—dark reference value).

Fiber optic cables 5, 5a and 5b may be replaced with hollow waveguides of a type well known in the art, to provide a more efficient delivery of light from tunable laser 1 to fiber terminus 10.

In operation, computer 4 cycles tunable illumination source 1 through a range of wavelengths. A sample, located on stage 7, is illuminated through one or more fiber terminals 10 by the tuned illumination. Data is collected via camera 9 and sent to personal computer 4 for normalization with respect to the illumination reference value detected by reference detector 3 or reference detector(s) 11. Thus, the images collected at each wavelength, when combined, provide a complete spectral image hypercube of the sample wherein each pixel of the hypercube contains the optical intensity spectrum across the sampled wavelength range for a particular spatial position.

Figure 4:
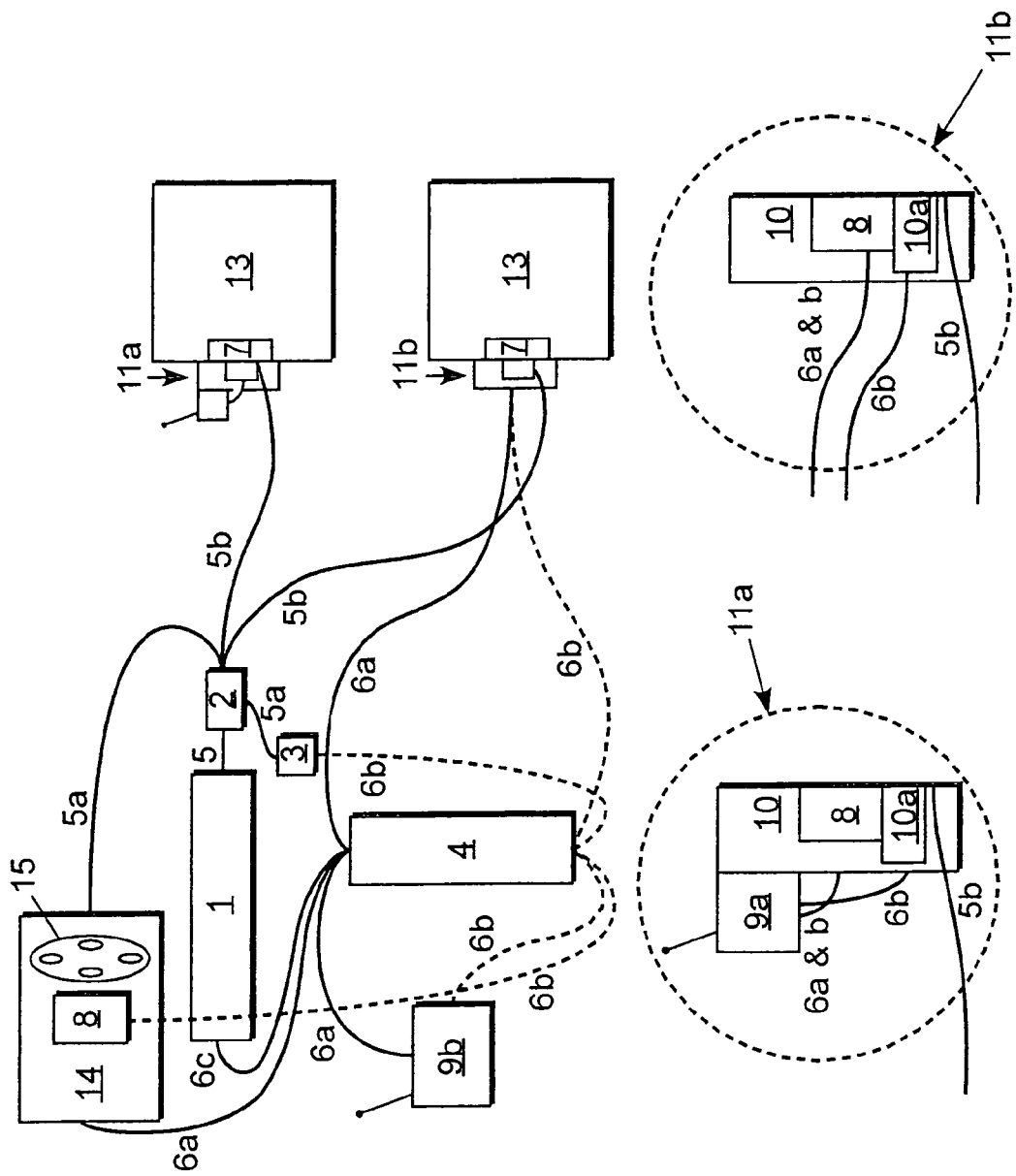
FIG. 4 shows a second embodiment of the invention used as a process monitoring apparatus

A second embodiment of the invention, shown in schematic form in FIG. 4, can be used to monitor the manufacture of a fungible commodity by monitoring the intensity of light reflected from, transmitted by, scattered by, or emitted by the commodity when exposed to various wavelengths of infrared light. In this embodiment, the imaging apparatus is replaced by a single-point photo detection device which can monitor the intensity of light reflected from the commodity when exposed to infrared light at various discrete wavelengths as produced by tunable laser 1. For purposes of this patent, including the claims, the term "reflected", used with respected to light used to illuminate a sample, is intended to mean light which is "reflected, transmitted, scattered or emitted" from the sample when exposed to a source of illumination.

The apparatus is very similar to the apparatus of the chemical imaging device described above. Tunable laser 1 can provide laser light over a range of wavelengths. The wavelengths produced by tunable laser 1 is controlled by computer 4 via commands sent over cable 6c. In an alternate embodiment, multiple tunable lasers may be used for redundancy or to enhance the speed of the process by having computer 4 control the lasers to emit tuned light of various wavelengths in a sequential or alternating manner. For purposes herein, however, the term "tunable laser" is meant to include embodiments utilizing one or more tunable laser source(s).

Fiber optic 5 delivers the output of tunable laser 1 to a beam splitter 2 which is as described above with respect to the imaging apparatus. Beam splitter 2 may in actuality be multiple beam splitters as it may be appropriate to monitor a manufacturing process at a plurality of different locations 13. Cables 5b conduct light from a series of beam splitters 2 to each individual location 13 within the manufacturing facility. The actual number of beam splitters 2 required is dependent upon the number of desired monitoring locations 13. Cables 5a deliver a light to reference detector 3 and continuous external qualification unit 14.

While it is necessary that the tuned laser light be delivered to monitoring locations 13 via fiber optic cable, the data returned from the monitoring devices may be delivered via either a wired connection 6b as shown in enlarged portion 11b of FIG. 4 or via an RF connection as shown in enlarged portion 11a of FIG. 4. The RF connection consists of RF transceiver 9a, located at each of said monitoring locations 13 and RF transceiver 9b coupled to computer 4. The RF connection may bi-bidirectional to send commands to terminus 11a and also to receive data therefrom.

Monitoring point 13 typically contains a fungible commodity such as, for example, a particular formulation of gasoline at a oil refining facility. Access to the commodity is provided through sample interface 7 which is typically a sapphire window. Reference 10 in FIG. 4 is an optics positioning block which positions fiber optic cable 5b carrying tuned laser light in a position to illuminate the sample contained in monitoring point 13 through sapphire window 7. Remote detector 8 is a photo resistive device capable of measuring the intensity of light reflected from the commodity at a variety of different infrared wavelengths, and is preferably a mercury cadmium telluride (MCT) detector which operates in a near infrared range.

Control commands may be sent to monitoring point 10 via cables 6a either directly from computer 4 or indirectly from computer 4 through RF transceiver 9b. Data is returned to computer 4 via cable 6b via either a hardwired connection or through RF tranceiver 9b. Reference 10a in FIG. 4 references a point of use reference detector which is used in a manner very similar to the point of use reference detectors described above with respect to the imaging apparatus. The data collected by computer 4 may be corrected to compensate for deviations in expected results from data collected by reference detectors 10a. Alternatively, the fiber termini may be utilized as described in FIG. 3, wherein the reference detector is integrated with the fiber terminus.

Continuous external standard qualification unit 14 comprises a variety of reference samples (which may include reference standard materials) and a photo detector 8 identical to that used in optics positioning block 10 at each monitoring point 13. The samples may be continuously selected via commands from cable 6c and the reference value is returned via cable 6b from photo detector 8. The reference information collected from continuous external qualification unit 14 and from the point of use detectors 10a is used in a manner similar to those used with respect to the imaging apparatus above wherein continuous corrections are made to the data by computer 4 to account for variations in the apparatus due to age, temperature, condition, etc. Optics positioning blocks 10 may also contain a temperature sensing unit which can monitor the temperature of the commodity at monitoring point 13.

Specific embodiments of the invention that have been presented herein are merely exemplary of the invention. Other embodiments or modifications of the embodiments presented are contemplated as being within the scope of the invention, as claimed below.

We claim:

1. A process monitoring system comprising:
one or more tunable light sources;
a light delivery medium for delivering light of a specific tuned wavelength from said tunable light sources to one or more terminals;
one or more reference detectors for detecting the intensity ratio of said tuned light at said tunable light source and one or more points along said light delivery medium and at one or more of said terminals;
one or more detectors, for detecting light reflected from or emitted by one or more samples located in close proximity to said one or more terminals, and
a controller for tuning said tunable light sources in a predetermined pattern; and
a data collection device for collecting and storing information from said detectors,
wherein said controller and said data collection device normalize said stored information with respect to any combination of reference value readings from said one or more reference detectors, and provide light source intensity normalization such that each plane or wavelength of data within a spectral hypercube is normalized to the reference value.

2. The process monitoring system of claim 1 wherein said tunable light sources are lasers capable of being tuned to generate light of a specific wavelength.

3. The process monitoring system of claim 2 wherein said specific wavelength is within the near infrared band.

4. The process monitoring system of claim 2 wherein said specific wavelength is within a band selected from spectral regions consisting of infrared, near infrared, visible and ultraviolet radiation.

5. The process monitoring system of claim 2 wherein said light delivery medium is selected from a group consisting of fiber optic cables and hollow wave guides.

6. The process monitoring system of claim 5 wherein said detectors are photo resistive devices, charge-coupled devices, and charge-injection devices.

7. The process monitoring system of claim 6 wherein said detectors detect the intensity of light reflected by, transmitted through, scattered from or emitted by said one or more samples.

8. The process monitoring system of claim 1 wherein said light delivery medium comprises:
one or more beam splitters coupled to said one or more tuned light sources; and two or more discrete pathways coupled to said splitters for the delivery of tuned light from said splitters to said one or more of terminals.

9. The process monitoring system of claim 1 wherein each of said one or more terminals comprises a positioning block for positioning said light delivery medium and said detector such that said tuned laser light is directed to said sample and light reflected from said sample is directed to said detector.

10. The process monitoring system of claim 9 wherein each of said one or more terminals includes one of said reference detectors for detecting the intensity of light emitted by said light delivery medium.

11. The process monitoring system of claim 9 wherein said one or more reference detectors includes a source reference detector configured to detect the intensity of tuned light as it leaves said tuned light sources.

12. The process monitoring system of claim 11 wherein said source reference detector is coupled to said light delivery element via one or more said beam splitters.

13. The process monitoring system of claim 9 wherein said controller and said data collection device is a computer.

14. The process monitoring system of claim 13 wherein said computer is coupled to said tunable light source and instruct said tunable light sources to tune their outputs to a given discrete wavelengths within a predefined band of wavelengths.

15. The process monitoring system of claim 14 wherein said computer sequences said tunable light sources through a predefined series of wavelengths.

16. The process monitoring system of claim 15 wherein said computer sequences said one or more tunable light sources in a sequential or alternating manner.

17. The process monitoring system of claim 13 wherein said computer is coupled to said one or more detectors and captures data from said one or more detectors and stores said data on a storage medium.

18. The process monitoring system of claim 17 wherein said data captured from said one or more detectors represents the intensity of light reflected by, transmitted through, scattered by or emitted from said one or more samples respectively.

19. The process monitoring system of claim 17 wherein said computer is coupled to said one or more detectors via a hard wired connection.

20. The process monitoring system of claim 17 wherein said computer is coupled to said one or more detectors via an RF connection comprising:
an RF transmitter located in close proximity to each or said one or more terminals; and
an RF receiver coupled to said computer.

21. The process monitoring system of claim 13 wherein said computer normalizes said data collected from said one or more detectors with respect to any combination of readings from said one or more reference detectors.

22. The process monitoring system of claim 21 wherein said computer detects noise generated by other components in the system and correct said stored data to eliminate the effect of said noise.

23. The process monitoring system of claim 22 wherein said noise is detected by collecting data from said one or more detectors absent any illumination and subtracting the collected data from data collected for each wavelength used to illuminate said one or more samples.

24. The process monitoring system of claim 13 further comprising a continuous external standard qualification unit comprising:
a terminal for delivering light emitted from said one or more tunable light sources;
a plurality of reference samples; and
a detector for detecting the intensity of light reflected from said plurality of reference samples under a light of varying wavelengths.

25. The process monitoring system of claim 24 wherein said computer applies a correction to said collected data to compensate for deviations in the expected intensity of light reflected from various ones of said plurality of reference standards.

26. A process monitoring system comprising:
a near infrared tunable laser;
a light delivery medium for delivering one or more pathways of light from said tunable laser to a sample, wherein said light delivery medium ends in a terminus;
one or more reference detectors for detecting the intensity ratio of said tuned light at said tunable laser source and at one or more points along said light delivery medium and at said terminus of said light delivery medium;
a detector for detecting the intensity of light in the near infrared band which is reflected by, transmitted through, scattered by or emitted from said sample; and
a computer, coupled to said tunable laser for controlling the wavelength of light output by said laser and coupled to said detector, for capturing and storing data representing intensity readings from said detector when said sample is illuminated under light at a variety of wavelengths, wherein said reference detectors are coupled to said computer, and wherein said computer normalizes said stored data with respect to any combination of reference value readings from said one or more reference detectors, and provides source intensity normalization such that each plane or wavelength of data within a spectral hypercube is normalized to the reference value.

27. The process monitoring system of claim 26 further comprising one or more beam splitters for splitting said light delivery medium into multiple pathways or for attaching said reference detectors at said various points.

28. The process monitoring system of claim 27 wherein said light delivery medium delivers light to a plurality of locations and further comprising a detector and a reference detector at each of said plurality of locations.

29. A method of monitoring the quality of a substances comprising the steps of:
controlling a tunable light source to sequentially emit light at a variety of discrete wavelengths;
illuminating said substance at one or more monitoring points with said light emitted by said tunable light source;
detecting the intensity ratio of said tuned light with one or more reference detectors at said tunable light source and at one or more monitoring points;

collecting data representing the intensity of light reflected by, transmitted through, scattered by or emitted from said substance at each of said discrete wavelengths;

normalizing said collected data with respect to any combination of reference value readings from said one or more reference detectors and providing source intensity normalization such that each plane or wavelength of data within a spectral hypercube is normalized to the reference value; and analyzing said collected data to determine if said substance is correctly formulated.

30. The method of claim 29 further comprising the steps of:
collecting data from one or more reference detectors; and
collecting said collected data to compensate for deviations from expected data collected from said reference detectors.

* * * * *

UNITED STATES PATENT AND TRADEMARK OFFICE
CERTIFICATE OF CORRECTION

PATENT NO.        : 7,528,950 B2                                            Page 1 of 1
APPLICATION NO.   : 11/033332
DATED             : May 5, 2009
INVENTOR(S)       : James K. Drennen, III, Carl A. Anderson and Robert P. Cogdill It is certified that error appears in the above-identified patent and that said Letters Patent is hereby corrected as shown below:

At Column 8, claim 29, line 56, change "substances" to --substance--.

Signed and Sealed this

Twelfth Day of October, 2010

David J. Kappos
*Director of the United States Patent and Trademark Office*